United States Patent [19]

Senger

[11] Patent Number: 4,725,538
[45] Date of Patent: Feb. 16, 1988

[54] METHOD OF ASSAYING THE PRESENCE OF CANCER CELLS

[75] Inventor: Donald R. Senger, Medfield, Mass.

[73] Assignee: The Beth Israel Hospital Association, Boston, Mass.

[21] Appl. No.: 791,349

[22] Filed: Oct. 25, 1985

[51] Int. Cl.$^4$ ................ G01N 33/554; G01N 33/574; G01N 33/577

[52] U.S. Cl. .......................................... 435/7; 435/29; 436/519; 436/530; 436/548; 436/813; 436/824

[58] Field of Search ...................... 435/7, 29; 436/519, 436/530, 547, 548, 813, 824

[56] References Cited

U.S. PATENT DOCUMENTS 4,469,787 9/1984 Woods ............................ 436/828 X

OTHER PUBLICATIONS

Elias, L. et al., J. Biol. Chem., 260 (11), 7023–7028 (1985).
"Differential Effect of Plasma Fractions from Normal and Tumour-Bearing Rats on Nuclear RNA Restriction", Nature, vol. 256, Aug. 7, 1975; Dorothy E. Schumm et al.
"A Major Phosphoprotein Marker for Neoplastic Transformation of Fibroplastic and Epithelial Cells", B. B. Asch et al.; Cold Spring Harbor Conferences on Cell Proliferation, vol. 9, Growth of Cells in Hormonally Defined Media, 1982, Cold Spring Harbor Laboratory.
"Absence of the Cancer-Associated Factor with a Molecular Weight of 60,000 from the Plasma of Patients with a Spectrum of Nonneoplastic Conditions", Dorothy E. Schumm et al.; Cancer Research 44, 401–406, Jan. 1984.
"Understanding Breast Cancer/Phosphoproteins as Markers of Neoplastic Progression in Mammary Cells; Bonnie B. Asch, et al., AMC Cancer Research Center and Hospital, Denver, CO., Marcel Dekker, Inc. 1983.
"Putative Transformation-Dependent Proteins in the Blood Plasma of Tumor-Bearing Rats and Cancer Patients"; Dorothy E. Schumm et al., Cancer Research 42, pp. 4964–4969, Dec., 1982.
"Transformation-Specific Secreted Proteins", Donald R. Senger et al.; Cold Spring Harbor Symposia on Quantitative Biology, vol. XLIV, 1980 Cold Spring Harbor Lab.
"A Secreted Phosphoproteinmarker for Neoplastic Transformation of both Epithelial and Fibroblastic Cells", Donald R. Senger et al., Reprinted from Nature, vol. 302, No. 5910, pp. 714–715. Apr. 1983.
"Transformed Mammalian Cells Secrete Specific Proteins and Phosphoproteins", Donald R. Senger et al., Cell, vol. 16, 885–893, Apr. 1979.
"Transformation-Specific Secreted Phosphoproteins"-/Macmillan Journals Ltd. 1980, Donald R. Senger et al., Nature, vol. 286, No. 5773, pp. 619–621, Aug. 7, 1980.

Primary Examiner—Sidney Marantz
Attorney, Agent, or Firm—Lorusso & Loud

[57] ABSTRACT

Method to detect and/or determine the presence of cancer cells in mammals, including humans, and to monitor the progress of treatment for cancer. A human protein marker, the assay-marker, has been ascertained of the molecular weight 70,000–74,000, which is secreted by cancer cells at levels 10-fold or greater than that observed with normal cells. An assay is described where the assay-marker or an antigenically analogous protein, the analog-marker, is used to prepare antibodies to the assay-marker. The antibodies are then reacted with blood or serum samples to determine the level of the assay-marker in the sample. Thus, the assay essentially comprises (1) providing an antibody to the protein described above (2) reacting the antibody of step 1 with the sample to be tested and (3) measuring the level of the reacted antibody to detect and/or determine the presence and/or quantity of cancer cells.

3 Claims, No Drawings

METHOD OF ASSAYING THE PRESENCE OF CANCER CELLS

BACKGROUND OF THE INVENTION

This invention relates to a method for diagnosing the presence of cancer and monitoring the progress of treatment of cancer patients, and more particularly, to a method of assaying the presence and quantity of cancer cells in a patient by quantitation of a circulating marker protein.

The identification of tumor markers has been an important objective of cancer research over the past several decades. Circulating tumor markers, i.e. markers released into the bloodstream, have been sought in particular because there are numerous clinical situations wherein it would be advantageous to detect and/or determine the presence of cancer cells in a patient by quantitation of a tumor marker in a plasma or serum sample derived from whole blood. One situation is a threshhold diagnosis to ascertain if there are any cancer cells in the patient. Another situation arises during treatment when it is very useful to monitor the changes in overall cancer cell presence to evaluate and guide the course of treatment. It is essential that the marker to be assayed for be one which is not secreted or secreted in insignificant amounts by non-cancerous cells. It is additionally of great practical importance, in order that the test have broad usefulness, that the marker to be assayed be one which is secreted by all or at least a large class of cancerous or transformed cells.

Circulating tumor markers such as carcinoembryonic antigen and alpha-fetoprotein are currently used to detect the presence of colon and liver carcinomas, respectively, and more particularly, they are used to monitor the effectiveness of treatment and recurrence of tumor growth. The applicability of carcinoembryonic antigen and alpha-fetoprotein is limited to a few tumor types, however, and no marker has been previously identified that detects a wide variety of tumor types. See generally, Sell, S. Alphafetoprotein. In: S. Sell (ed.) Cancer Markers, pp 249-293. Clifton, N.J.: Humana Press, 1980 and, in the same text, Shively, J. E. and Todd, C. W., Carcinoembryonic antigen A: chemistry and biology, at pp. 295-314.

SUMMARY OF THE INVENTION

In accordance with the present invention, a protein has been discovered which largely meets the requirements for a suitable marker for a test as described above. This protein is secreted by transformed cells, i.e., cancer cells, at levels 10-fold or greater than that observed with untransformed or normal cells. Furthermore, it has been found that this protein is secreted by a wide variety of tumor cell types and that it circulates in the blood. This protein, which is assayed in accordance with the present invention to detect and/or determine the presence of cancer cells, is referred to hereinafter as the "assay-marker".

With these findings in mind, an assay has been developed which detects and/or determines the presence of the assay-marker in a blood or serum sample from a patient. This, in turn, indicates the presence and/or quantity of cancer cells in the patient. The method of the assay comprises (1) providing an antibody to the protein described above (2) reacting the antibody of step 1 with the sample to be tested and (3) measuring the level of the reacted antibody to detect and/or determine the presence of cancer cells.

It is therefore an object of the present invention to provide a method to detect and/or determine the presence of cancer cells in a patient.

It is a further object of the present invention to provide a method which monitors the changes in overall cancer cell activity to evaluate and guide the course of treatment.

It is still another object of the present invention to provide an assay to detect and/or determine the presence of cancer cells which assays for a protein which is not secreted or secreted in insignificant amounts by non-cancerous cells.

It is a further object of the present invention to provide an assay for a protein which is secreted by all or at least a large class of cancerous or transformed cells.

DETAILED DESCRIPTION OF THE INVENTION

A protein has been discovered which is secreted in insignificant amounts by untransformed or normal cells and at levels 10-fold or greater by transformed or cancer cells. The molecular weight of this human protein, as determined by polyacrylamide gel electrophoresis, is approximately 70,000–74,000. The protein reacts with antibody raised by rabbits against the 62,000 MW antigenically analogous rat protein marker (analog-marker). The protein (assay-marker), and its analogous rat protein marker (analog-marker), are cleaved by purified thrombin to fragments of molecular weight approximately 30,000. The assay-marker and the analog-marker are both cleaved in the course of whole blood coagulation to fragments of approximately 30,000 MW.

Moreover, it has been found that the both analog-markers and assay-markers bind to barium citrate. Over 98% of serum or plasma proteins do not bind to barium citrate. The proteins also bind completely to a DE 23 cellulose column in 0.01M $Na_2HPO_4$, pH 6.8. They elute completely as the NaCl concentration is raised to 0.4–0.5M in 0.01M $Na_2HPO_4$ pH 6.8.

It has been determined that the assay-marker is present in a relatively low quantity in normal human plasma. It is, however, present in greatly elevated levels, as compared to the normal human plasma, in the malignant human pleural and ascites effusions, and in plasma of patients with disseminated cancers. It is also present in culture medium of various human cell tumor lines, such as MNNG-HOS, KHOS/NP and HT1080, all available from the American Type Culture Collection, Rockville, Md. (ATCC). It is also found in human milk at 20 times the levels of normal serum or plasma.

With these characteristics and sources in mind, an assay has been developed to detect the presence of the protein, the assay-marker, in a serum or plasma sample from a patient. Indication of the presence of the assay-marker then indicates the tumor burden in the patient.

The method of the assay comprises (1) providing an antibody to the protein described above (2) reacting the antibody of step 1 with the sample to be tested and (3) measuring the level of the reacted antibody to detect and/or determine the presence of cancer cells.

I. PREPARATION OF THE ANTIBODY

Generally, preparation of an antibody involves selecting a source of the protein to be assayed for (the assay-marker) or of an antigenically analogous protein (the analog-marker). After the secreted proteins are purified, an antiserum which is the source of the antibody is prepared, generally by immunization of an animal with the protein. If the antibody is prepared from the human assay-marker, it will recognize the human assay-marker in a sample. If, however, the antibody is prepared from an analog-marker, it is necessary to subsequently confirm that the antibody recognizes the corresponding assay-marker secreted by human tumor cells.

Initially, a cell line was ascertained which secreted the protein in amounts greater than all other cell lines. The temperature sensitive (ts) B77 Rat 1 BIH cell has been found to secrete the rat analog-marker profusely. Because this cell line is not generally available, it was deposited with the ATCC as deposit number CRL 8912 on Oct. 8, 1985.

The cells are grown to confluence at 34° C. in the presence of a medium and a serum or serum-like supplement or even a completely defined medium like salts or hormones. They are grown to confluence only because growing them to confluence is more efficient and economical. More cells per square centimeter are obtained. Most preferred for the growth medium is Dulbecco's Modified Eagle's Medium (DMEM) and 5% fetal calf serum and approximately 7% $CO_2$.

The confluent cells are washed, optimally three times, in serum-free DMEM and incubated overnight in serum-free DMEM. A range of 16 to 24 hours is optimal. The serum-free DMEM in which the cells were cultured overnight, the "conditioned medium" is centrifuged to remove cells and any particulate debris and then passed over an anion exchange cellulose column. Centrifuging at 10,000 xg for 10 minutes is optimal. The DE-23 cellulose, manufactured by Whatman Inc., Chemical Separation Division, Clifton, N.J., is one useful column. Generally approximately 1400 ml of the conditioned medium is passed over a freshly prepared cellulose column (approximately 50 ml volume) which has been equilibrated with phosphate-buffered saline (PBS). This process generally takes 16 hours. All the analog-marker binds to the column. The column is then washed with 200 ml of 0.25M NaCl in 0.01M sodium phosphate, pH 7.0. The analog-marker is then eluted with 100 ml of 0.4M NaCl in 0.01M sodium phosphate, pH 7.0 to form the "crude purificate".

At this point the analog-marker is not pure, but it is by far the major protein in this fraction, and is clearly visible on SDS polyacrylamide (7.5% w/v) slab gels as the major band on the gel, having a broad band with mobility corresponding to a molecular weight of approximately 62,000.

Electrophoretic separation on sodium dodecyl sulfate (SDS) polyacrylamide gel provides an improved method to ascertain the presence of this antigen. In addition, final purification of the analog-marker may be effected by this method. This procedure is generally described in U.K. Laemmli: Cleavage of Structural Proteins during the Assembly of the Head of Bacteriophage T4, *Nature*, 227: pp. 680–685, August, 1970, and has been modified for the purposes of this invention.

A separation gel is formulated from a 7.5% (w/v) solution of acrylamide with 0.2% (w/v) N,N'-bis-methylene acrylamide, 0.375M TRIS-HCl (pH 8.8), and 0.1% (w/v) SDS. A stacking gel is formulated from a 3.0% (w/v) solution of acrylamide, 0.08% N,N'-bis-methylene acrylamide, 0.125M TRIS-HCl pH 6.8, 0.1% (w/v) SDS. Both gels are polymerized by addition of 0.025% v/v tetramethyl-ethylenediamine and ammonium persulphate. For the purposes of this invention, the gels are formed in slabs 14 cm by 16 cm and 1.5 mm thick. An electrode buffer (pH 8.3) is used which consists of 0.025M Tris, 0.192M glycine, and 0.1% SDS. The crude purificate is introduced into a solution which will be referred to as "final sample buffer" of composition 0.0625M Tris-HCl (pH 6.8), 2% (w/v) SDS, 10% glycerol, 0.1M dithiothreitol, 0.001% bromophenol blue. The final sample buffer with crude purificate is heated to 90° C. for 1.5 minutes prior to electrophoresis. Electrophoresis was conducted toward the anode with a current of 40 ma per slab until the bromophenol dye reached the bottom of the slab (about 2 hours).

The slab gels are then stained. There are a variety of methods which may be used. Preferred for the purposes of this invention is Coomassie blue staining, which is easy and works well in this application. The gel is immersed in a solution of 25% v/v isopropyl alcohol, 2-propanol, 10% v/v acetic acid, 65% v/v water and 0.025% (w/v) Coomassie Brilliant Blue (R-250). The next day, the gel is destained in 10% v/v acetic acid, 90% v/v water to visualize the protein bands.

The molecular weight markers used on polyacrylamide slab gels are:

| Source | Protein | Molecular weight |
|---|---|---|
| rabbit muscle | Phosphorylase b | 94,000 |
| bovine serum | albumin | 67,000 |
| egg white | ovalbumin | 43,000 |
| bovine erythrocyte | carbonic anhydrase | 30,000 |

These may all be obtained from Pharmacia Fine Chemicals Division of Pharmacia Inc., Piscataway, N.J. 08854.

The secreted analog-marker is then purified. Any method for purification may be used; the two methods below are particularly useful in the present invention.

The 100 ml of partially purified analog-marker is next dialyzed against PBS and passed over a 1 ml hydroxylapatite column (obtained from BioRad, Chemical Division, Richmond, Calif.) which has been equilibrated with PBS. All of the analog-marker binds to the column. This column is eluted successively with 3 ml volumes of the following: PBS, 0.1M sodium phospate pH 6.8, 0.2M sodium phosphate pH 6.8, 0.3M sodium phosphate pH 6.8, 0.4M sodium phosphate pH 6.8, 0.5 M sodium phosphate pH 6.8. The bulk of the analog-marker is usually recovered in the 0.3M and 0.4M sodium phosphate fractions but sometimes substantial amounts are found in the 0.2M or 0.5M fractions. For this reason, it is essential to perform an electrophoretic analysis of the various eluted fractions from the hydroxylapatite column. Aliquots (100 μl) of the various fractions are electrophoresed on a SDS polyacrylamide (7.5% w/v) slab gel and the gel is stained, as described above. The analog-marker is identifiable as the major protein band with a mobility corresponding to a molecular weight of 62,000.

A second method to effect purification of the analog-marker is the following procedure. This method is easier to perform and is preferred. 1400 ml of the conditioned medium is mixed with 0.1 of its volume of 3.8% sodium citrate solution plus 0.1 of its volume of 15% (w/v) barium chloride solution and then incubated at 4° C. for 30 minutes. After incubation the mixture is centrifuged at 10,000 xg for 20 minutes (at 4° C.) and the supernatant discarded. The precipitate is redispersed in a 15% (w/v) solution of barium chloride (4° C.) and the dispersion centrifuged for 10 minutes (4° C.). The supernatant is discarded and the precipitate is redispersed in distilled water (4° C.). The dispersion is centrifuged at 10,000 xg for 10 minutes and the supernatant is discarded. The analog-marker is eluted with approximately 12 ml of a solution of 0.2M sodium citrate, pH 6.8, dialyzed against PBS, reprecipitated with 0.1 volume of 3.8% (w/v) sodium citrate and 0.1 volume 15% barium chloride. The precipitate is washed as before with barium chloride and $H_2O$ and the analog-marker eluted again with 2.0 ml of 0.2M sodium citrate pH 6.8. Approximately 18 ml of PBS is added to the 2 ml elute and the mixture, now 20 ml, is dialyzed against PBS and vacuum concentrated to approximately 1-2 ml. This forms the "crude purificate".

After either of the above purification procedures, a final purification is performed by electrophoresing, as described above, on SDS polyacrylamide slab gels (7.5% w/v) and stained as before. The purest fractions from the first inital purification method are pooled and electrophoresed. All of the fraction obtained from the second initial purification method is electrophoresed if that method is chosen. The analog-marker is again visible as the major band with mobility corresponding to a molecular weight of approximately 62,000. It is believed that the analog-marker is actually at least 3 proteins with a very similar electrophoretic mobilities, but the three bands are not always completely resolved and hence appear as one somewhat broad band (about 0.4 cm in width).

The region of the polyacrylamide slab gel that contains the analog-marker or assay-marker is excised from the remainder of the gel, and the gel slice bearing the markers is subsequently homogenized in PBS. Typically, 300-500 μg of the markers is derived from 1400 ml of conditioned ts B77 Rat 1 BIH medium, cultured at 34° C.

Once the assay-marker or the analog-marker has been derived and purified, an antibody must be prepared to it. To prepare an antibody, there are a vast number of possible immunization schemes that are likely to work and a variety of animals that could be a potential source of antibody. Any of these methods may be used to prepare an antibody to the human protein of interest. In addition, it may be possible to derive monoclonal antibodies to the protein of interest here.

Antibodies to the assay-marker or the analog-marker can be raised by immunization of rabbits. If so, New Zealand White rabbits (available from Pine Acres Rabbitry, W. Brattleboro, Vt.) are used.

As a preliminary to innoculation, each rabbit is bled to obtain a supply of pre-immune serum for reference.

Purified rat analog-marker prepared as described above in Step I and containing about 200 μg of the protein is mixed with an equal volume of Complete Freund's Adjuvant to obtain a homogeneous suspension of about 8 ml. A rabbit is inoculated subcataneously and intradermally with this suspension in approximately 12 dorsal sites.

Three weeks from the initial innoculation, the innoculations are repeated but using Incomplete Freund's Adjuvant in place of the Complete Adjuvant.

Three weeks later, the innoculations using Incomplete Freund's Adjuvant are again repeated.

After a further three weeks, blood is drawn from the rabbit to provide the serum which is the antibody source.

If the antibody source is raised against the rat analog-marker, it is necessary to run a confirmatory test of its reactivity with the human analog of the protein, the assay-marker. For analysis of human serum samples, only antisera that crossreacts with the assay-marker are of any use. There are probably many ways to screen rabbit antisera for reactivity with the assay-marker, any of which may be used. The following method is preferred.

MNNG-HOS, available from ATCC, are used for the assay, although other human cell lines could be used as well (e.g. KHOS/NP, HT1080). MNNG-HOS cells, which are of human origin, secrete the human assay-marker. Cells are cultured under standard conditions, for example, DMEM, 10% fetal calf serum, and approximately 7% $CO_2$, washed 3 times with serum-free phosphate-free DMEM, and labeled in the presence of the same with approximately 300 μCi/ml carrier-free $^{32}P$-orthophosphate. After approximately 3-4 hours, the culture medium containing $^{32}P$-labeled proteins is removed and subjected to "immunoprecipitation" with the antisera to be tested.

Typically, 10 μl of rabbit serum is added to a tube containing 300 μl of culture medium from $^{32}P$-labeled cells, mixed, incubated for 30 minutes. Antigen-antibody complexes are then isolated by adsorption to fixed *Staphylococcus aureus*. The preferred method to accomplish this isolation is described in S. W. Kessler: Rapid Isolation of Antigens from Cells with a Staphylococcal Protein A-Antibody Adsorbent: Parameters of the Interaction of Antibody-Antigen Complexes with Protein A, *The Journal of Immunology*, 115: 1617-1624, December 1975. Utilizing that method in the present invention, 150 μl of a 10% v/v solution of fixed *Staphylococcus aureus* (Cowan 1 strain), which can be obtained from The Enzyme Center, Inc., Malden, Mass. 02148, is added. The contents of the tube are mixed and incubated for approximately 30 minutes. The *Staph. aureus* pellet which has bound the antigen-antibody complexes is collected by low speed centrifugation (approximately 200 xg) for 10 minutes and washed and centrifuged successively 3 times with PBS. The pellets are then suspended in 100 μl of the final sample buffer, heated and electrophoresed on slab gels as described above. The gels are fixed, stained, and dried and then subjected to autoradiography with presensitized Kodak X-Omat R film and a Dupont Cronex Intensifying Screen at 70° C. The films are processed according to manufactures recommendations—exposure times required are typically 3 days to 7 days. See generally, Laskey and Mills, *Febs Letters*, 82: 314-316, 1977.

Samples representing $^{32}P$-labelled culture media incubated with antiserum from a rabbit that bears antibodies that crossreact with the assay-marker will reveal a major $^{32}P$-labelled protein band with an electrophoretic mobility corresponding to a molecular weight of approximately 70,000-74,000. Immunoprecipitation with pre-immune serum will not result in precipitation of such a band nor will immunoprecipitation with antiserum that does not react with the human protein of interest.

In summary, antiserum that recognizes the human assay-marker of interest will bring about the precipitation of a 70,000-74,000 MW, $^{32}P$-labelled protein from the culture medium of MNNG-HOS cells ($^{32}P$-orthophosphate labeled) when used in the above immunoprecipitation assay, which involves electrophoretic and autoradiographic analysis.

As an alternative to the immunization scheme presented above, monoclonal antibodies to the protein of interest may be derived. Using the techniques generally described in *Hybridoma Techniques*, ©1980 by Cold Spring Harbor Laboratory, Cold Spring Harbor, N.Y., ISBN 0-87969-143-3, mouse monoclonal antibodies may be prepared to the assay-marker in the following way.

First, Balb/c mice, which can be obtained from the Animal Genetics and Production Branch of the National Cancer Institute, are immunized with the purified analog-marker from the ts B77 Rat 1 BIH cells of Step I. There are a variety of ways to do this; the following is a common approach. Three animals will be immunized at a time.

The animals are injected subcutaneously with 100 μg of analog-marker which is emulsified as a 1:1 mixture in Complete Freunds Adjuvant. After 4–6 weeks, the animals are injected intravenously with 1–10 μg of analog-marker for three consecutive days.

On the day following the third intravenous injection, the immunized mice will be killed by cervical dislocation, their spleens will be removed sterilely, and spleen cells will be prepared as described on page 6 of *Hybridoma Techniques*.

The cells are then fused to a mouse myeloma cell line. A variety of the myeloma cell lines are available for fusion. I intend to use the mouse myeloma cell line P3X63 Ag8.653 which is available from the ATCC.

Fusion of the mouse spleen cells with the mouse myeloma cells will be carried out as described on page 10 of *Hybridoma Techniques*. All of the solutions or media required are described on pages 5–6 of that manual. Preparation of the peritoneal cells for the feeder layers is described on page 6 on the manual. A supernatant of the growing hybrid cells is obtained.

The supernatant of the growing hybrids is tested for an antibody that reacts with the protein of ts B77 Rat 1 BIH cells by radioimmunoassay (RIA) and enzymeimmunoassay (EIA). These procedures are described on pages 21–26 of *Hybridoma Techniques*.

Cell populations producing antibody to the analog-marker will be expanded by in vitro culture and subjected to cloning as described on pages 11–12 or pages 14–15 of *Hybridoma Techniques*. The clones so obtained will be expanded, and supernatants from the monoclonal populations will be tested for the antibody by RIA and EIA.

The antibodies must then be screened for reactivity with the human assay-marker. The screening process described above is used, with the following modifications.

100 μl of the hybridoma supernatant containing monoclonal marker with 300 μl of the culture medium from the $^{32}$P-labelled MNNG HOS cells is incubated for 30 minutes. Next, 25 μl of affinity purified rabbit anti-mouse immunoglobulin is added. Preparation of the affinity rabbit anti-mouse immunoglobulin is described on pages 21–22 of *Hybridoma Techniques*. Following that procedure, the *Staph. aureus* is added and the remainder of the screening technique is performed as described above.

Again, hybridoma supernatants containing monoclonal antibody that binds the assay-marker, molecular weight 70,000–74,000, will result in precipitation of this protein. Precipitation of the protein will be visualized by gel electrophoresis and autoradiography. Clones producing the desired antibody will be expanded in culture.

II. The Assay

The assay to determine the presence of cancer cells in a patient can be performed using either serum or plasma samples. For example, 0.5 ml samples may be used. Samples may be kept frozen at −70° C. prior to the assay. Plasma samples should be derived from blood taken in 3.8% (w/v) sodium citrate. There are probably many methods for assaying for the presence of the assay-marker which utilize the antibody produced. The following is one method useful for the purposes of this invention.

The assay-marker contained in the samples is first partially purified by adsorption to barium citrate. To a 0.5 ml sample of plasma is added 0.1 volume of 15% (w/v) barium chloride solution and mixed. Serum samples are treated by first adding 1/10 volume of 3.8% (w/v) sodium citrate followed by adding 1/10 volume of 15% (w/v) barium chloride. In either case, the mixture is incubated for 30 minutes at 4° C. to form a precipitate of barium citrate and bound protein, including any assay-marker present. The precipitate is collected by centrifuging for 5 minutes at 10,000 xg, 4° C., then washed with a solution of 15% (w/v) barium chloride (4° C.), recollected by centrifugation as before, washed with distilled water (4° C.), and recollected by centrifugation as before. The assay-marker is eluted from the barium citrate pellet with 250 μl of electrophoresis final sample buffer supplemented with sodium citrate to 0.2M and heated to 90° C. for 1 minute. The eluted protein, including the assay-marker of interest, is then separated from the barium citrate pellet by centrifugation (10,000 xg for 5 minutes).

The supernatant obtained is then electrophoresed on a polyacrylamide gel, the gel and the procedure are described above. It is expedient to process multiple samples, for example by using 10 parallel lanes on the slab using a scheme in which samples from patient A are loaded on lanes 1 and 10, samples from patient B loaded on lanes 2 and 9, samples from patient C loaded on lanes 3 and 8, samples from patient D on lanes 4 and 7 and pre-stained molecular markers loaded on lanes 5 and 6. The pre-stained molecular markers are available from Bethesda Research Laboratories, Inc. They are as follows:

| | |
|---|---|
| Myosin (H-chain) | 200,000 |
| Phosphorylase B | 92,500 |
| Bovine Serum Albumin | 68,000 |
| Ovalbumin | 43,000 |
| alpha-chymotrypsinogen | 25,700. |

One of the replicated halves of the slab will be used for a control as described below.

The antibody is then reacted with the prepared sample. This can be done directly on the slab gel. However, it is more expedient to react them on a material which the antibody and assay-marker cannot penetrate. One such material is nitrocellulose paper. The antibodies and assay-markers remain on the surface of the paper and readings can be taken more easily. Thus, after electrophoretic separation is completed, and the bromophenol blue tracking dye has reached the bottom of the slab, the proteins are electrophoretically transferred to nitrocellulose paper following essentially the procedure described in Towbin et al: *Proc. Natl. Acad. Sci.* USA, Vol. 76, No. 9, pp 4350–4353, September 1979. More particularly, the gel slab is prepared for transfer by equilibrating for 1 hour in a solution of: 0.025M Tris, 0.192M glycine, 20% v/v methanol, at pH 8.3. The transfer is carried out in a Hoeffer transfer apparatus at 20v (current 0.1 to 0.2 amp) with the nitrocellulose sheet facing the anode and using buffer solution of the same composition as the equilibrating solution described above. The transfer is carried out for approximately 16 hrs. Following the transfer, the nitrocellulose sheet is removed and incubated in a solution of 3% (w/v) hemoglobin for 1 hour to block it.

To conduct the immunoassay, the nitrocellulose sheet is cut in half, the first half containing the material originating in lanes 1–5 of the gel slab, the second half containing material originating in the duplicate lanes 6–10. The first half is treated with 22 ml of a solution of 3% (w/v) hemoglobin with 100 μl of the reaction confirmed serum, the antiserum that crossreacts with or binds the human assay-marker, and incubated for 1 hour. The treated sheet is then washed with multiple changes for 2 hr. in a solution of 0.05% v/v Tween 20 in PBS. The washed sheet is then labeled, preferably by incubating with 50 μl of $^{125}$I-protein A in 22 ml of 3% (w/v) hemoglobin for 1 hour. $^{125}$I-protein A reagent with 8 μCi/ug activity is commercially available from Dupont NEN Products, Albany Street, Boston, Mass. The labeled sheet is then washed for 24 hours with repeated changes of a solution of 0.05% v/v Tween 20 in PBS. The second half of the nitrocellulose sheet is treated in exactly the same manner except using pre-immunization serum from the same rabbit.

The labeled sheets are dried and put back together and subjected to autoradiography with presensitived X-Omat R film using a Cronex intensifying screen at −70° C. for an approximately 4 day exposure.

To interpret the plasma samples, the relative quantity of the assay-marker in the sample, and of the corresponding tumor burden in the patient, is indicated by the degree of exposure of a band at nominal molecular weight 70,000–74,000 on the film derived from the nitrocellulose sheet treated with the immune rabbit serum. (Estimates of molecular weight are made with reference to the molecular weight markers in lanes 5 and 6.) Comparison with the corresponding area of the control (derived with the use of pre-immune serum) permits distinguishing response specific for the assay-marker above non-specific background response. The assay is quantitated by scanning the film with a laser densitometer coupled to an integrator. Specific activity of the 70,000–74,000 weight band from a clinical sample is compared with an average sample from a normal health pool. The clinical response can then be expressed as a factor against normal response.

The interpretation of serum samples is the same as that of the plasma samples except that the tumor burden of the patient is indicated by the sum of the degree of exposure of a band at nominal molecular weight 30,000 and the band at nominal molecular weight 70,000–74,000. This is because the assay-marker is cleaved in the course of blood coagulation when the serum is derived from whole blood to fragments with nominal molecular weight 30,000. It is believed that this cleavage is due to thrombin.

Clinical Results

Blood plasma or serum samples from patients diagnosed as having various cancerous and non-malignant conditions and from healthy volunteers have been assayed with the above-described procedure. The results are summarized in the following table.

| Patient Diagnosis | No. of Patients | Test Results |
|---|---|---|
| Disseminated cancers: | | |
| Teratocarcinoma | 3 | +,+,+ |
| Prostate carcinoma | 4 | +,+,+,+ |
| Stomach carcinoma | 1 | + |
| Colon carcinoma | 2 | +,+ |
| Pancreatic carcinoma | 2 | +,+ |
| Breast carcinoma | 2 | +,+ |
| Lung carcinoma | 3 | +,+,+ |
| Mesothelioma | 1 | + |
| Ovarian carcinoma | 1 | + |
| Hepatoma | 1 | + |
| Small localized tumor: | | |
| Colon carcinoma | 2 | −,− |
| Bladder carcinoma | 1 | − |
| Leukemias and Lymphomas:* | | |
| Lymphoma | 3 | −,−,+ |
| CML | 2 | −,+ |
| APL | 2 | −,+ |
| AML | 2 | −,+ |
| Non-cancerous Conditions | | |
| Liver disease | 1 | − |
| Renal failure | 1 | − |
| Gram-Negative bacterial sepsis** | 5 | +,+,+,−,− |
| Infectious mononucleosis | 1 | − |
| Early pregnancy | 1 | − |
| Late pregnancy | 1 | − |
| Factor VII deficiency | 1 | − |
| Factor X deficiency | 1 | − |
| Bacterial infections | 1 | − |
| No Pathology | 6 | all − |

Results code: A + indicates a response of 4X or greater than that of normal healthy volunteers. A − indicates a response equal to normal healthy volunteers. A response of 1X is the averaged response for non-pathological samples.
*It is believed that the chemotherapy treatment interfered with the assay.
**Blood-borne bacterial infections have shown positive results for unknown reasons.

To indicate the usefulness of the assay for monitoring the course of cancer treatment, readings were taken both before and after treatment. A patient with disseminated prostate carcinoma (included in the table) originally had an assay of 7X. He was treated with chemotherapy over a period of four months following his original test. At the end of this treatment, clinicians judged the patient's tumor load to be greatly reduced. A test at the end of the period gave an assay of 1.7X, corresponding well with the clinical evaluation.

Pleural and ascites malignant fluids from patients with malignancies have also been tested, and gave assays in the range of 5X to 40X compared to corresponding fluids accumulated as a result of non-cancerous conditions.

It is apparent that many modifications and variations of this invention as herinbefore set forth may be made without departing from the spirit and scope thereof. The specific embodiments described are given by way of example only and the invention is limited only by the terms of the appended claims.

What is claimed is:

1. A method of assaying the presence of cancer cells in a patient by measuring the level of assay-marker in a sample from the patient, comprising:

(a) providing an antibody to the human analog of a protein secreted by the cell line ts B77 Rat 1 BIH, which cell line is deposited with the American Type Culture Collection, Rockville, Md. as deposit number CRL 8912, and wherein the assay-marker has the following characteristics:
  (1) molecular weight 70,000–74,000;
  (2) reacts with an antibody raised in rabbits directed against the rat analog-marker having a molecular weight of 62,000;
  (3) cleaved by thrombin to fragments having an approximate molecular weight of 30,000;
  (4) cleaved in the course of whole blood coagulation to fragments having a molecular weight of 30,000;
  (5) binds to barium citrate; and
  (6) binds to an anion cellulose column completely in 0.01M $Na_2HPO_4$ at pH 6.8 and is eluted with 0.4M NaCl;
(b) reacting the antibody of step (a) with the sample to be tested; and
(c) measuring the level of reacted antibody to detect and/or determine the presence and/or quantity of cancer cells in the patient.

2. The method of claim 1 wherein the antibodies prepared in step (2) are monoclonal antibodies.

3. The method of claim 1 wherein the step of preparing the antibody further comprises cross-reacting said antibody with the human assay-marker to confirm the antibody's reactivity with the assay-marker.

* * * * *